United States Patent [19]

Yamasaki

[11] Patent Number: 5,181,526
[45] Date of Patent: Jan. 26, 1993

[54] ELECTRODE FOR HUMAN HEART PACEMAKER

[75] Inventor: Haruki Yamasaki, Isehara, Japan

[73] Assignee: Tanaka Kikinzoku Kogyo K.K., Japan

[21] Appl. No.: 688,032

[22] Filed: Apr. 19, 1991

[30] Foreign Application Priority Data

Apr. 20, 1990 [JP] Japan .................. 2-104554
Apr. 20, 1990 [JP] Japan .................. 2-104555

[51] Int. Cl.⁵ .............................................. A61N 1/05
[52] U.S. Cl. ............................ 128/784; 128/419 P
[58] Field of Search ........................ 128/784-786, 128/419 P, 419 D

[56] References Cited

U.S. PATENT DOCUMENTS

| | | | |
|---|---|---|---|
| 4,149,542 | 4/1979 | Thorén | 128/419 P |
| 4,156,429 | 5/1979 | Amundson | 128/419 P |
| 4,408,604 | 10/1983 | Hirshort et al. | 128/419 P |
| 4,440,178 | 4/1984 | Bussard et al. | 128/784 |
| 4,542,752 | 9/1985 | Dehaan et al. | 128/784 |
| 4,602,637 | 7/1986 | Elmqvist et al. | 128/419 P |
| 4,603,704 | 8/1986 | Mund et al. | 128/784 |
| 4,677,989 | 7/1987 | Robblee | 128/419 P |
| 4,762,136 | 8/1988 | Baker, Jr. | 128/786 |
| 4,844,099 | 7/1989 | Skalsky et al. | 128/785 |
| 5,005,587 | 4/1991 | Scott | 128/419 P |
| 5,044,375 | 9/1991 | Bach, Jr. et al. | 128/786 |

Primary Examiner—Lee S. Cohen
Assistant Examiner—J. Jastrzab
Attorney, Agent, or Firm—Klauber & Jackson

[57] ABSTRACT

Disclosed herein is an electrode for human heart pacemaker comprising an electrode substrate prepared by Pt or a Pt alloy, Ti or a Ti alloy and a mixture of platinum and a platinum group metal oxide coated thereon, the upper portion of the electrode being comprised of mesh or porous.

Since the physical dimensions of the electrodes can be made smaller, the substantial surface area can be made larger and the catalytic performance can be elevated because of the coating on the electrode of the present invention. The electrode has remarkably low polarizability, a high response characteristic from a human heart, low electric consumption, smaller input impedanco and extremely high reliability.

Also disclosed is an implantable mesh electrode comprising a Pt/Ti composite prepared by coating Ti with Pt.

1 Claim, 1 Drawing Sheet

ELECTRODE FOR HUMAN HEART PACEMAKER

BACKGROUND OF THE INVENTION

The present invention relates to an electrode for human heart pacemaker, and to an electrode employed in the field of medical equipment, more in detail to an implantable mesh electrode, especially an electrode for reanimation (defibrillator).

A human heart pacemaker comprises a main element, an electric wire and an electrode. The performance required for an electrode especially for an implantable electrode for human heart pacemaker includes that polarizability of pulses generated from the pacemaker is low, impedance (input impedance) of signals is low when the signals from a human heart are detected, and impedance (output impedance) is high when the signals are supplied to the human heart, in addition to that the electrode can be easily adhered to the human heart. Although, accordingly, the improvements of the polarizability and the input impedance of the electrode which is formed by Pt or a Pt alloy having high electric conductivity and being harmless to a living body have been implemented by decreasing the dimension of the electrode and the polarizability for increasing the output impedance and by mechanically roughening the surface, the sufficient effects have not yet been obtained especially in connection with the polarizability and the input impedance.

Although, the further improvements have been implemented which comprises coating a mixture of Pt and a platinum metal oxide on an electrode formed by Pt or a Pt alloy, or Ti or a Ti alloy to prepare the electrode for a human heart pacemaker, much further improvements are being requested.

Further, heretofore, a mesh electrode has been employed which is formed by wire rods of Pt-Ir(10%) or Ti in the viewpoint of its electric characteristics and its suitability to human organs in the field of medical equipment or the like. However, the electrode possesses the below drawbacks.

Although the Pt-Ir(10%) possesses better electric conductivity and excellent electrode characteristics, it is inferior to the mesh electrode made of Ti in fatigue characteristics against repeated stress of heart pulsations.

Although, on the other hand, Ti is superior in such mechanical characteristics as fatigue strength and tensile strength, the Ti is made brittle by absorbing a hydrogen gas generated in humors acting as an electrolyte by means of a current during the working of the electrode.

SUMMARY OF THE INVENTION

The present invention has been made to overcome the above problems. An object of the invention is to provide an electrode for a human heart pacemaker having minimum dimension and input impedance.

Another object is to provide an electrode having smaller polarizability which promotes the prevention of erroneous working of the pacemaker, the extension of a cell life and the response characteristics of the heart.

A further object of the invention is to provide an implantable mesh electrode possessing excellent fatigue characteristics and anti-brittleness.

The present invention is an electrode for human heart pacemaker comprising an electrode substrate prepared by Pt or a Pt alloy, Ti or a Ti alloy and a mixture of platinum and a platinum group metal oxide coated thereon, the upper portion of the electrode substrate being comprised of mesh or porous.

Since the physical dimensions of the electrodes can be made smaller, the substantial surface area can be made larger and the catalytic performance can be elevated because of the coating according to the electrode of human heart pacemaker of the present invention, the electrode having remarkably low polarizability, high response characteristic from a human heart, low electric consumption, smaller input impedance and extremely high reliability can be obtained.

The other aspect of the invention is an implantable mesh electrode comprising a Pt/Ti composite prepared by coating Ti with Pt.

Since the implantable mesh electrode of the present invention is made of the Pt-Ti composite formed by the Ti coated with Pt, the electrode enables to prevent from obtaining brittleness by means of hydrogen absorption, and possesses the excellent mechanical characteristics of Ti and the excellent electrode characteristics of Pt so that an implantable electrode of high reliability having a long life can be obtained.

DETAILED DESCRIPTION OF THE INVENTION

According to the electrode for human heart pacemaker having the mesh-like porous upper portion, the substantial surface area of the electrode is made to be larger, the polarizability is made smaller, the input impedance is made much more smaller and the adherability of heart tissue to a heart wall upon the growth thereof is made more excellent. The affinity between the electrode prepared by coating a mixture of platinum and a platinum group metal oxide on an electrode substrate formed by platinum or a platinum alloy, titanium or a titanium alloy, and a hydrogen ion and a chlorine ion in humors is small, and the ability of the electrode to discharge these ions is excellent so as to further decrease the polarizability and the impedance effectively.

Further, since the material of the electrode substrate is limited to the platinum, the platinum alloy, the titanium or the titanium alloy, the electrode is harmless to a living body and possesses high electrical conductivity. Since the coating material is limited to the platinum and the platinum group metal oxide, the adhere strength between the coating layer and the substrate is high.

A coating method may be any one of the conventional coating methods and includes a physical vapor deposition method, a chemical vapor deposition method, a baking method, a flame coating method, and a plating method and the like. The entire surface is not required to be coated with the mixture, the coating onto the portion of the surface which is in contact with humors is sufficient. The thickness of the coating is not less than 0.5 $\mu$m, and it has been confirmed that the said thickness provides the sufficient catalytic performance.

Figure 1:
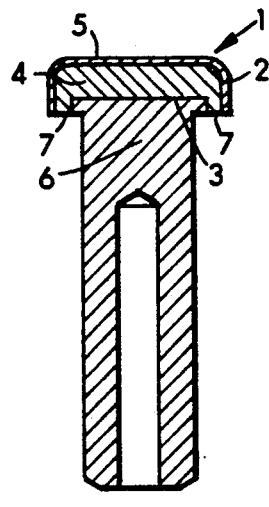
FIG. 1 shows one example of an electrode for human heart pacemaker of the present invention.

Referring now to FIG. 1, one example of an electrode for human heart pacemaker of the present invention is illustrated.

An electrode for human heart pacemaker 1 essentially consists of an upper electrode core member 4 having a lower concave 3 and a cylindrical leg 6 an upper portion of which is engaged with the concave 3. The upper portion 2 of the core member 4 is covered with a mesh 5. The mesh at the outer periphery 7 of the engaged portion is fused and joined by means of laser welding to prepare the electrode substrate.

Figure 2:
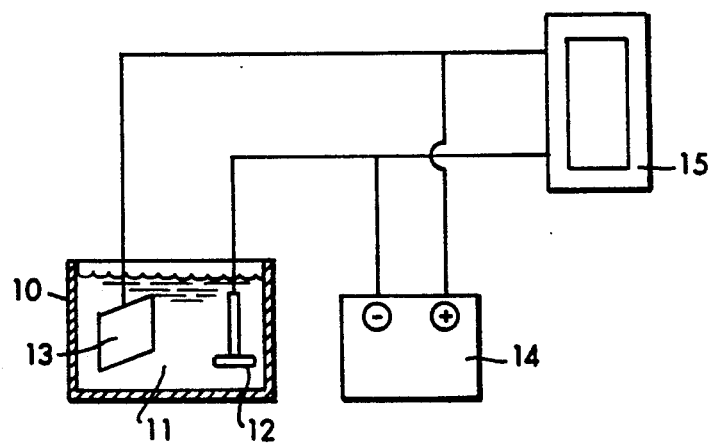
FIG. 2 shows a test circuit for measuring polarizability.

FIG. 2 is a test circuit employed in Examples and Comparative Examples for measuring the polarizability from their pulse shapes in which 10 denotes an electrolytic cell and a solution 11 consists of 1 g of NaCl, 1 liter of water and 1 liter of ethanol. A cathode 12 in the solution is the electrode for human heart pacemaker, an anode 13 is a titanium plate having a surface area of 12 $cm^2$ and its interelectrode distance is 50 mm. 14 denotes a constant current source supplying a current of 10 mA, and 15 denotes an oscilloscope for measuring a pulse shape.

Figure 3:
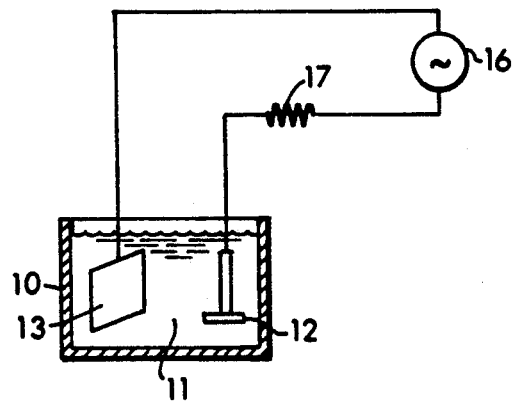
FIG. 3 shows a test circuit for measuring input impedance.

FIG. 3 is a test circuit employed in Examples and Comparative Examples for measuring the input impedance in which numerals 10 to 13 denote the same elements as those in FIG. 3, and the description is omitted. 16 denotes an electric source of 100 mV and 50 Hz, and 17 denotes a shunt resistance of 10 Ω for measuring the input impedance.

According to the above implantable mesh electrode of the invention, since the electrode is a Pt-Ti composite formed by coating Ti which is liable to be made brittler by means of hydrogen absorption with Pt possessing excellent electrode characteristics as an outer coating, the implantable mesh electrode provided with the excellent mechanical characteristics of Ti and the excellent electrode characteristics of Pt can be obtained.

One of the reasons Pt is employed as the outer coating is its joining strength when coated to the Ti because the sufficient mechanical strength can be provided by Ti.

Any coating method including such a dry plating method as vapor deposition and sputtering, a wet plating method employing cladding material such as extruded material or a pipe. While the coating thickness usually requires not less than 1 μm from the viewpoint of the coating effect, the thickness may be appropriately determined considering the high price of Pt which is a precious metal. The shape of the electrode is not restricted to a wire rod, and any material formed by Pt-coated Ti can be employed.

EXAMPLES

The present invention will now be described in detail in connection with the following Examples.

EXAMPLE 1

At first, an upper electrode core member having a lower concave was prepared by press-molding a mesh made of Pt-Ir(10%) and having 300 mesh and a wire diameter of 0.02 mm. The core member was covered with a mesh made of Pt-Ir(10%) and having 150 mesh and a wire diameter of 0.05 mm so that the lower concave and a cylindrical upper leg were engaged with each other. The mesh at the outer periphery of the engaged portion was fused and joined by means of laser welding to prepare an electrode substrate before coating having an upper electrode diameter of 2 mm, an upper electrode thickness of 0.5 mm, a lower electrode diameter of 1.5 mm and a lower electrode thickness of 3.5 mm. Then, the upper portion of the core member (electrode head) was electrolytically corroded employing a NaCl-hydrochoric acid solution, and chloroplatinic acid and iridium chloride were weighed for obtaining a mixture having a ratio of Pt-Ir(75%). After the mixture was dissolved in butanol, it was applied by brush to the electrode substrate while defoaming bubbles generated on the mesh by means of a blower. After drying at 100° C., the substrate was baked in atmosphere at 550° C. for ten minutes. The application, the drying and the baking were repeated 30 times to obtain an electrode for human heart pacemaker as shown in FIG. 1. The thickness of the coating was 1 μm.

EXAMPLE 2

Titanium particles having a particle diameter of 0.05 mm were centered and molded at a temperature of 1100° C. to prepare a semicircular member having a concave at the lower portion thereof having a bulk density of 2.7 g/$cm^3$. The semicircular member was covered with a titanium mesh having 150 mesh and a wire diameter of 0.05 mm, and the lower concave 3 of the upper electrode core member and the cylindrical upper leg were engaged with each other. The mesh at the outer periphery of the engaged portion was fused and joined by means of laser welding to prepare the electrode substrate before coating shown in FIG. 1 having the same dimensions and shape.

Then, after the surface of the upper electrode portion was etched in a hot oxalic acid solution, chloroplatinic acid and iridium chloride were weighed for obtaining a mixture having a ratio of Pt-Ir(33%). After the mixture was dissolved in butanol, it was applied by means of spray to the electrode substrate. After drying at 100° C., the substrate was baked in oxygen having a partial pressure of 1 atmospheric pressure at 500° C. for ten minutes. The application, the drying and the baking were repeated 10 times to obtain an electrode for human heart pacemaker as shown in FIG. 1. The thickness of the coating was 0.7 μm.

COMPARATIVE EXAMPLE 1

The same electrode for human heart pacemaker as that of Example 1 having the same dimensions, shape and materials except that no coating was formed on the upper electrode portion was prepared.

COMPARATIVE EXAMPLE 2

An electrode for human heart pacemaker made of titanium was prepared having an upper electrode substrate diameter of 2 mm, an upper electrode substrate thickness of 0.5 mm, a lower electrode substrate diameter of 1.5 mm and a lower electrode substrate length of 3.5 mm.

The respective polarizability and the input impedances of the thus obtained electrodes for human heart pacemaker of Examples 1 and 2 and Comparative Examples 1 and 2 were measured to obtain results shown in Tables 1 and 2. The polarizability was measured from their pulse shapes employing the above test circuit shown in FIG. 2, and the input impedance was measured employing a test circuit shown in FIG. 3.

Figure 4:
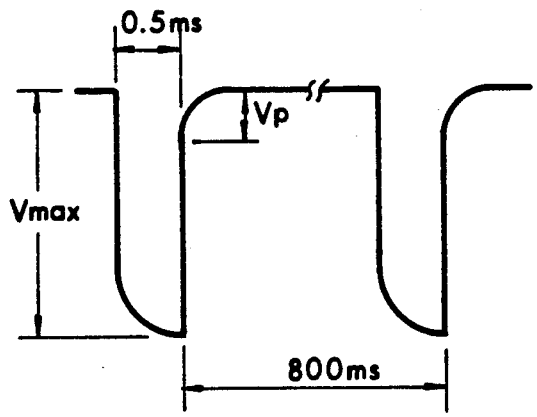
FIG. 4 shows a pulse shape employed for calculating the polarizability.

The polarizability can be calculated according to the below equation employing Vmax and Vp of a pulse shape shown in FIG. 4.

Polarizability (%) = $(V_p/V_{max}) \times 100$

The input impedance can be calculated as follows.

Input Impedance (Ω) = (Supply Voltage)/(Circuit Current) = 1000/(Measured Voltage)

TABLE 1

| Sample | Polarizability (%) | Input Impedance (Ω) |
|---|---|---|
| Example 1 | 3.7 | 360 |
| Example 2 | 5.2 | 440 |

TABLE 2

| Sample | Polarizability (%) | Input Impedance (Ω) |
|---|---|---|
| Comp. Example 1 | 20.7 | 610 |
| Comp. Example 2 | 24.8 | 960 |

As is apparent form Tables 1 and 2, it is found that the electrodes for heart pacemaker of Examples 1 and 2 have remarkably lower polarizability than those of the electrodes of Comparative Examples 1 and 2, and smaller input impedances.

EXAMPLE 3

A mesh electrode having 50 mesh and dimensions of 30 mm×50 mm was prepared by employing a Pt-Ti composite wire having 5 μm of Pt thickness and 0.1 mm of wire diameter.

The Pt-Ti composite wire was prepared as follows.

At first, after 0.5 μm of Pt was plated on the surface of a rod-like member made of Ti having an outer diameter of 4.75 mm, the rod-like member was inserted into a pipe member made of Pt having an outer diameter of 5.4 mm and an inner diameter of 4.85 mm. In order to expel air existing between the rod-like member and the pipe member, the composite was elongated under vacuum and its outer diameter was reduced to 2.5 mm by means of a hot swaging processing. Thereafter, the wire drawing and the intermediate heat treatment (in nitrogen) were repeated to obtain a Pt-Ti composite wire having a wire diameter of 0.1 mm.

COMPARATIVE EXAMPLE 3

A mesh electrode similar to that of Example having 50 mesh and dimensions of 30 mm×50 mm was prepared employing a Ti wire (Japanese Industrial Standards No. 2) having a wire diameter of 0.1 mm.

COMPARATIVE EXAMPLE 4

A mesh electrode having 50 mesh and dimensions of 30 mm×50 mm was similarly prepared employing a Ti wire (Japanese Industrial Standards No. 2) having a wire diameter of 0.1 mm.

Electrolysis was carried out by means of an electric current of 2 A in an electrolyte consisting of 19 g of NaCl, 1000 cc of $H_2O$ and 1000 cc of an alcohol employing the above mesh electrode as a cathode and a plate electrode made of Ti having the dimensions of 30 mm×40 mm as an anode. The respective mesh electrodes before and after the electrolysis were subjected to a 90° bending test and the number of times of the bending which was required for generating a crack in the wire and the electric characteristic were summarized in the below Table 3.

As apparent from the foregoing, the mesh electrode employing the Pt-Ti composite wire possesses, even after the electrolysis, similar excellent fatigue characteristics to those of a mesh electrode made of Ti which cannot be obtained in a mesh electrode made of Pt wires, and low specific resistance.

TABLE 3

| | Number of Times of Bending | | Specific Resistance (Ω) |
|---|---|---|---|
| | Before Electrolysis Test | After Electrolysis Test | |
| Example 3 | $5 \times 10^7$ | $4 \times 10^7$ | 24.5 |
| Comp. Ex. 3 | $5 \times 10^5$ | $5 \times 10^5$ | 55 |
| Comp. Ex. 4 | $4 \times 10^8$ | $4 \times 10^4$ | 35 |

What is claimed is:

1. An electrode for a human heart pacemaker comprising an electrode substrate having an upper and lower portion, said electrode substrate formed of Pt, a Pt alloy, Ti or a Ti alloy, and a mixture of platinum and a platinum group metal oxide being coated thereon, the upper portion of the electrode being mesh or porous.